(12) United States Patent
Brehm et al.

(10) Patent No.: US 10,441,711 B2
(45) Date of Patent: Oct. 15, 2019

(54) DEVICE FOR CONNECTING A VIAL TO A CONTAINER OR TO A FLUID LINE AND TRANSFERRING THE CONTENTS OF A VIAL TO A CONTAINER OR A FLUID LINE AS WELL AS A METHOD FOR DOING SO AND USE OF SUCH A DEVICE

(71) Applicant: FRESENIUS MEDICAL CARE DEUTSCHLAND GMBH, Bad Homburg (DE)

(72) Inventors: Winfried Brehm, Hofheim (DE); Martin Kaiser, Hassfurt (DE); Massimo Fini, Mirandola (IT); Alain Veneroni, Spino D'Adda (IT)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 69 days.

(21) Appl. No.: 15/512,772

(22) PCT Filed: Sep. 15, 2015

(86) PCT No.: PCT/EP2015/071074
§ 371 (c)(1),
(2) Date: Mar. 20, 2017

(87) PCT Pub. No.: WO2016/041948
PCT Pub. Date: Mar. 24, 2016

(65) Prior Publication Data
US 2017/0304531 A1 Oct. 26, 2017

(30) Foreign Application Priority Data
Sep. 18, 2014 (DE) .................. 10 2014 013 892

(51) Int. Cl.
*A61M 5/14* (2006.01)
*A61J 1/20* (2006.01)
(Continued)

(52) U.S. Cl.
CPC .............. *A61M 5/1417* (2013.01); *A61J 1/20* (2013.01); *A61J 1/2013* (2015.05); *A61J 1/2037* (2015.05);
(Continued)

(58) Field of Classification Search
CPC .............. A61M 5/1417; A61M 1/3655; A61M 5/1689; A61J 1/2013; A61J 1/2037; A61J 1/2089
(Continued)

(56) References Cited

U.S. PATENT DOCUMENTS 5,647,845 A 7/1997 Haber et al.
2004/0210192 A1 10/2004 Degentesh et al.
2009/0163866 A1 6/2009 Hines et al.

FOREIGN PATENT DOCUMENTS

DE 102009051945 5/2011
EP 2319553 5/2011
(Continued)

*Primary Examiner* — Phillip A Gray
(74) *Attorney, Agent, or Firm* — Jacobson Holman, PLLC.

(57) ABSTRACT

A device and a method facilitate connecting a vial to a container or to a fluid, line, and transferring the contents of the vial to the container or to the fluid line. The device has a connecting device, a first holder for accommodating the connecting device, a second holder for accommodating the vial, and an actuating means. The connecting device includes an annular housing, an inside part having at least one puncture device, and a tube connection. The annular housing is configured to be rotatable about the inside part so as to function as a valve, so that by rotation of the annular
(Continued)

housing, flow paths of the connecting device can be opened and closed.

17 Claims, 12 Drawing Sheets

(51) Int. Cl.
 *A61M 1/36* (2006.01)
 *A61M 5/168* (2006.01)
 *A61M 5/162* (2006.01)
(52) U.S. Cl.
 CPC ........... *A61J 1/2072* (2015.05); *A61J 1/2089* (2013.01); *A61M 1/3655* (2013.01); *A61M 5/1415* (2013.01); *A61M 5/162* (2013.01); *A61M 5/1689* (2013.01); *A61M 2205/3317* (2013.01); *A61M 2205/6063* (2013.01)

(58) Field of Classification Search
 USPC .......................................................... 604/507
 See application file for complete search history.

(56) References Cited

FOREIGN PATENT DOCUMENTS

| | | | |
|---|---|---|---|
| EP | 2366324 | 11/2011 | |
| EP | 2462913 | 6/2012 | |
| WO | WO 01/49361 | 7/2001 | |
| WO | WO 01/91963 | 12/2001 | |
| WO | WO 2004/052725 | 6/2004 | |
| WO | WO 2010/146506 | 12/2010 | |
| WO | WO-2010146506 A1 * | 12/2010 | .......... A61M 5/1409 |
| WO | WO 2011/092068 | 8/2011 | |
| WO | WO 2011/141200 | 11/2011 | |

* cited by examiner

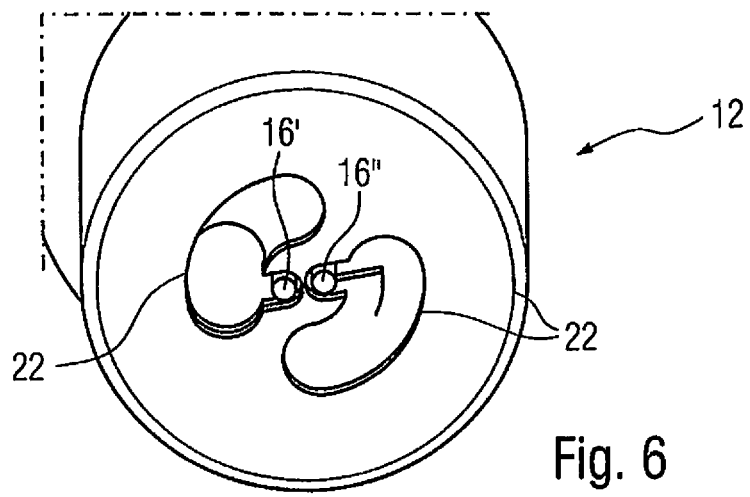
Fig. 6
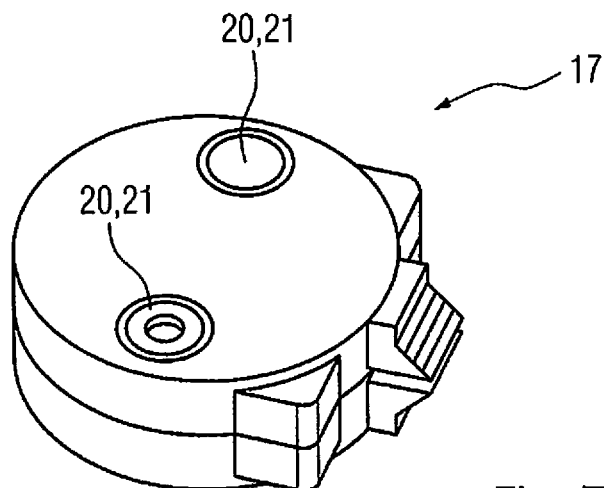
Fig. 7
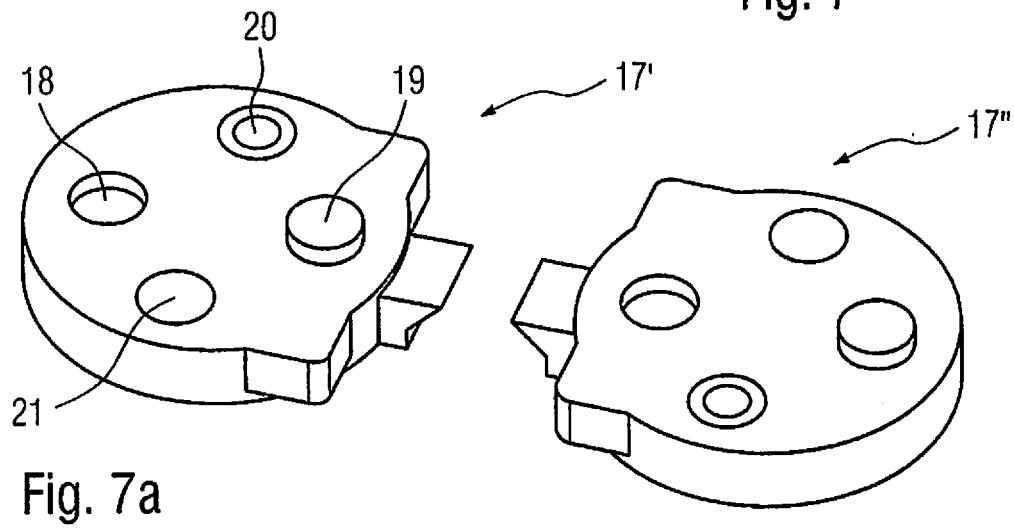
Fig. 7a
Fig. 7b

DEVICE FOR CONNECTING A VIAL TO A CONTAINER OR TO A FLUID LINE AND TRANSFERRING THE CONTENTS OF A VIAL TO A CONTAINER OR A FLUID LINE AS WELL AS A METHOD FOR DOING SO AND USE OF SUCH A DEVICE

BACKGROUND OF THE INVENTION

1. Field of the Invention

The invention relates to the field of transfer of fluids from one container to another container or to a fluid line or to a connecting device.

The invention relates to an apparatus for connecting a vial to a container or to a fluid line by means of a connecting device, which is suitable for this purpose, as well as a method for doing so. The invention also relates to the use of an apparatus for connecting a vial to another container or to a fluid line by means of a connecting device.

This apparatus is used mainly in the medical field for the administration of medications in an extracorporeal circulation. However, this reference does not mean a restriction; use in nonmedical fields is also conceivable.

Commercial vials, also known as injection vials, are small containers made of glass, sometimes plastic with a capacity of 1 mL to 200 mL which are used in medicine and in chemical laboratories.

They contain medicines or chemical substances in the form of a solution, suspension or dry solids usually in a highly concentrated dose. Filling with dry solids is used when the stability of a substance is too low. The dry solids are dissolved shortly before administration by adding sterile water or some other solvent.

Vials are sealed with a stopper or a membrane made of an elastic material, for example, rubber or polytetrafluoroethylene. Aluminum flanging secures the injection stopper or the puncture membrane to the head of the vial. These stoppers and/or membranes have the least thickness at the center, where they can be punctured easily with the help of a mandrel or a cannula.

In medicine in particular, there are various circumstances under which it is necessary to transfer the contents of a vial and in particular a medication from a vial into a container or a fluid line.

The transfer of a medicine contained in the vial into a container is performed for the purpose of dilution, for example, and transfer to a fluid line is used for therapeutic treatments by means of infusion or extracorporeal circulation.

The contents of a vial, for example, a medicine, may be removed by the clinic personnel by transferring the requirement amount first into a syringe.

For the purpose of dilution or for preparing a medication solution, the medication drawn up into a syringe is then transferred into another container.

In an infusion or an extracorporeal treatment, the medication drawn up into the syringe is administered into the fluid line which is provided for this purpose and is connected to the patient, usually by way of injection sites designed as T-pieces. Disadvantages of administering a medication from the vial with the help of a syringe include the time-consuming double transfer of the medication and the cost-intensive use of additional disposable materials, such as syringes and cannulas. Furthermore, administration through a syringe equipped with a cannula entails the risk of injury for the clinic personnel and the associated problems with regard to disposal.

In particular when using cytostatics, antiviral drugs, antibiotics and radiopharmaceuticals, there may be a threat to the medical or pharmacological personnel. It is therefore advantageous if suitable measures can reliably prevent the aforementioned substances from coming in contact with the user.

Aseptic handling of medications from vials is desirable not least of all when preparing medications to reliably rule out any contamination of the medications, which cannot be ensured when handling syringes.

When most medications are administered from a vial, they are in the form of a bolus. However, some therapeutic substances including anticoagulants (e.g., heparin, citrate), vitamins, antibiotics, erythropoietin or iron preparations (e.g., Venofer) are preferably administered over a longer period of time. In such a case, a manual injection is very time-consuming because the clinic personnel must be available over the entire period of time of the prolonged injection.

For extracorporeal treatment methods, such as hemodialysis, for example, most of the equipment therefore contains an infusion apparatus. Automatically controlled injection pumps are generally used as long-term infusion devices for heparin anticoagulant. However, these dosing pumps are not suitable for accommodating the usual vials, so their contents must first be transferred into suitable containers and so again a double transfer of the therapeutic substance must be performed.

Therefore, specially designed connecting devices are available, which are capable of accommodating the head of a vial with an accurate fit and have a mandrel for puncturing an opening through the stopper and/or the membrane of the vial, for connecting a vial to another container or to a fluid line.

2. Description of Related Art

Devices which serve the purpose of connecting vials to a container or a fluid line are already known from the prior art.

Unexamined German Patent DE 10 2009 051 945 A1 thus describes a system for administering medicines in an extracorporeal circulation. A connecting device establishes a direct connection of a commercial vial to the extracorporeal circulation while preventing any air from entering it. The connecting device comprises two line pathways, where the line path to the medication administration has a gas barrier element and the second line path is connected to an external gas reservoir, which may be air, a gas-filled container or a gas-filled line and which serves to ventilate the vial.

The document WO 01/91693 describes a device for connecting a connecting device to a vial. This device has a holding device for a vial in various sizes, a holding device for a connecting device in different sizes and actuating means for coupling the connecting device to the vial. In this coupling operation, the connecting device is pressed onto the neck of the vial, such that the puncture device of the connecting device penetrates through the septum of the vial.

The documents EP 2 319 553 and WO 2011/141200 disclose a tube set having a connecting device for coupling a puncture vial. The connecting device comprises a feed lumen for supplying a therapeutic substance and a vent lumen for supplying a fluid such as air or a liquid into the interior of the vial for displacing the therapeutic substance.

The connecting device described in the document EP 2 319 553 has a flow regulator by means of which the delivery rate of the therapeutic substance from the vial can be adjusted; it opens into a drip chamber, from which air penetrates into the vial.

The connecting device described in document WO 2011/141200 may also open into a drip chamber and has at least one one-way valve which is placed inside the feed lumen or inside the vent lumen and opens and closes under the influence of a pressure difference created by a pump.

The document WO 2011/092068 relates to a connecting device of the known type, which consists of a base body and a puncture device having two line paths parallel to one another, which are continued in the base body of the connecting device. Bulges on the blunt end of the puncture device close off the line paths when no vial is connected. When a vial is connected, the puncture device, which is slidingly supported in a perpendicular plane X is shifted and the line paths of the puncture device and of the base body are combined with one another.

The document EP 2 462 913 proposes a system for dispensing fluid, which comprises a vial and a suitable connecting device having a puncture device for opening the septum of the vial. Before connection, a cover capable of connecting the vial to the connecting device with an accurate fit is placed on the vial; this cover also has a gripping face with the help of which the cover can then be rotated in the connecting device for opening the flow paths.

The document WO 2010/146506 discloses a connecting device, which has a housing and a receptacle part with a puncture device. The flow path of the connecting device is opened by rotation of the receptacle part in the housing.

SUMMARY OF THE INVENTION

The invention is based on the problem of refining a device and a method of the aforementioned type so that a secure, time-saving and labor-saving means of transferring the contents of a vial into a container or a fluid line directly out of a standard commercial vial without using any additional aids, such as disposable syringes or pumps, for example, is made possible.

The invention is also based on the object of ensuring a septic handing to prevent contamination of the contents of the vial in transfer to a container or to a fluid line.

Another object of the invention is easy applicability of the device. It should be convenient to bring the connecting device and the vial together, so the individual steps for transferring the contents of the vial into a container or into a fluid line (combining the vial and the connecting device, opening the septum of the vial, opening and closing the flow paths) can be performed with the least possible effort and without any risk of injury for the personnel.

Another object of the invention is to make available a device and a method which will ensure that the connecting device and the vial are brought together in a defined position and are held securely and reliably for the duration of the application.

In addition, the device should be easily and inexpensively manufacturable.

This object is achieved according to the invention by the features described herein.

The device for connecting a vial to a container or to a fluid line and for transferring the contents of a vial to a container or a fluid line has a first holder which is suitable for accommodating a connecting device, a second holder which is suitable for accommodating a vial, an actuating means and a connecting device. The latter consists of an annular housing and an inside part with a puncture device, wherein the annular housing of the connecting device is designed to be rotatable about the inside part, so that the flow paths of the connecting device can be opened and closed by the rotation of the housing.

The connecting device may also be designated as an adapter or connector.

Advantageous embodiments of the invention are as described herein.

This object is also achieved by a method employing the inventive device, the method comprising the following steps:

Locking the connecting device in the first holder of the device for connecting a vial to a container or a fluid line, Locking the vial in the second holder of the device for connecting a vial to a container or a fluid line, Combining the vial and the connecting device by activating the actuation means, Opening and closing the flow paths of the connecting device by rotation of the housing about the inside part of the connecting device, Removal of the vial from the first holder and the connecting device from the second holder.

Advantageous embodiments of the inventive method are as described herein.

Also described herein is a medical technical treatment unit with the apparatus according to the invention.

Also described herein is a use of the apparatus according to the invention, which is suitable for use in the analytical, pharmaceutical and preferably medical fields.

And, also described herein is an evaluation unit for the apparatus according to the invention, which makes available information about the opening and closing of the connecting device by detecting the position of the vial and/or the connecting unit with the help of at least one sensor.

The apparatus according to the invention makes it possible to transfer the contents of a standard commercial vial directly into a container or a fluid line without having to use any additional disposable parts such as syringes or cannulas. This eliminates the problem of disposal, less time is required and there is no risk of injury for the personnel. Since the membrane of the vial is punctured automatically by the mandrel when the actuation means are activated, there is again no risk of injury for the personnel in this procedure. Furthermore, in this way there is a reliable connection of the vial for the duration of the administration, and transfer of the contents takes place under aseptic conditions.

The apparatus according to the invention also ensures easy applicability. The puncture vial and connecting device can be inserted into the apparatus with no problems and the force required to open the flow paths is reduced due to the rotation of the housing about the inside part.

After starting operation of the apparatus, the transfer of the contents of the puncture vial into a container or a fluid line takes place automatically, i.e., in a time-saving and labor-saving manner.

Due to the simple composition of the apparatus comprised of only a few parts, the apparatus according to the invention can be manufactured easily and inexpensively. The elimination of any additional disposable parts results in a further cost reduction.

BRIEF DESCRIPTION OF THE DRAWINGS

The invention will be explained in greater detail below with reference to the drawings, which show:

FIG. 6: a three-dimensional diagram of the inside part of the connecting device;

FIG. 7: a three-dimensional diagram of the gasket of the connecting device;

FIGS. 7a and b: a three-dimensional diagram of the two halves of the gasket of the connecting device;

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
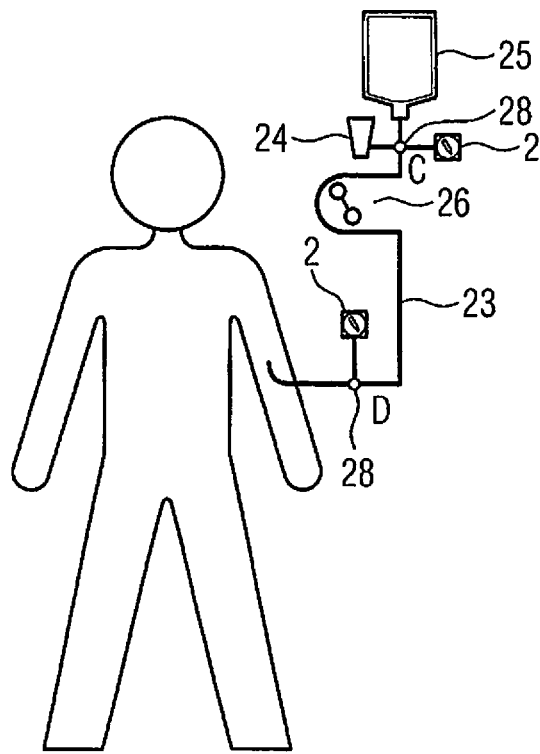
FIG. 1: a simplified schematic diagram of the structure of an infusion device having the apparatus according to the invention.

FIG. 1 shows a simplified schematic diagram of the structure of an infusion device into which the apparatus according to the invention can be integrated.

For infusion of a medical solution, a tube set [23], which is connected by a venous access to a patient, is used. The contents of an infusion container [25] flow through a drip chamber [24] with the aid of gravity into the patient or the contents are supplied to the drip chamber by a pump [26]. Injection sites [28] for drugs may be integrated into the tube set. These are suitable for connecting the apparatus according to the invention [2]. Connecting the apparatus according to the invention to the drip chamber [24] is also possible. The apparatus according to the invention may also be designed as an integral part of an infusion tube set.

Figure 2:
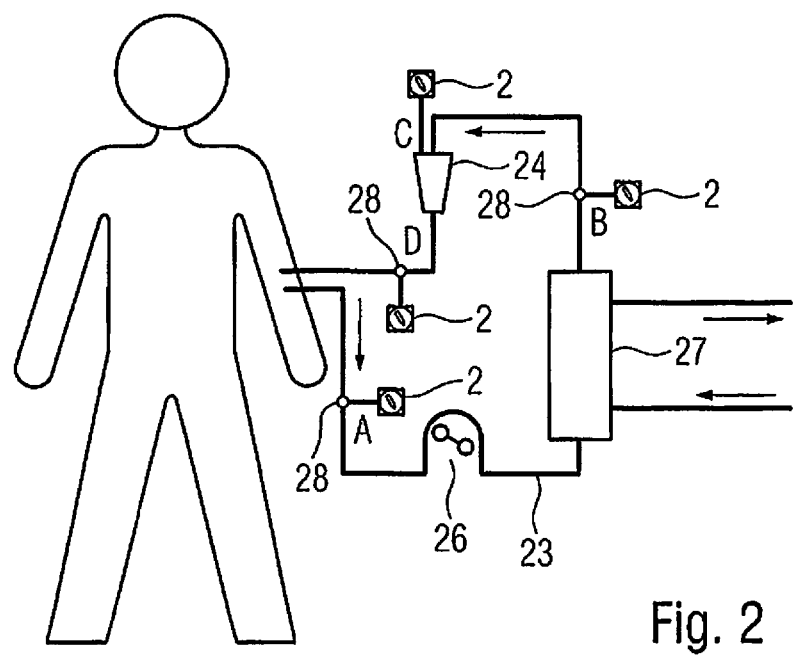
FIG. 2: a simplified schematic diagram of the structure of an extracorporeal treatment device having the apparatus according to the invention on the example of a hemodialysis machine.

FIG. 2 shows a simplified schematic diagram of the structure of an extracorporeal treatment device on the example of a hemodialysis machine into which the apparatus according to the invention can be integrated.

In hemodialysis, blood is taken from a patient usually through an arterial venous fistula. The part of the extracorporeal circulation upstream from the dialyzer is referred to as the arterial part and the part downstream from the dialyzer is the venous part. In hemodialysis, as with other extracorporeal treatment processes, the extracorporeal circulation usually takes place completely within a tube set or a cassette set [23]. In most cases, a drip chamber [24] is integrated into the venous part of the circulation to eliminate any air bubbles that might be formed. Injection sites [28] for drugs, which are suitable for connecting the apparatus according to the invention [2], are usually also provided in the tube sets and/or in the cassette sets for extracorporeal treatments. As shown in FIG. 2, it is possible to add drugs with the help of the apparatus according to the invention [2] to the arterial part of the extracorporeal circulation [A], to the venous part of the circulation upstream from the drip chamber [B] and downstream from the drip chamber [D] or to add the drugs to the drip chamber itself [C]. The apparatus according to the invention may also be an integral part of a tube set or a cassette set for an extracorporeal treatment, and preferably a hemodialysis tube set or cassette set may be designed that way.

Figure 3:
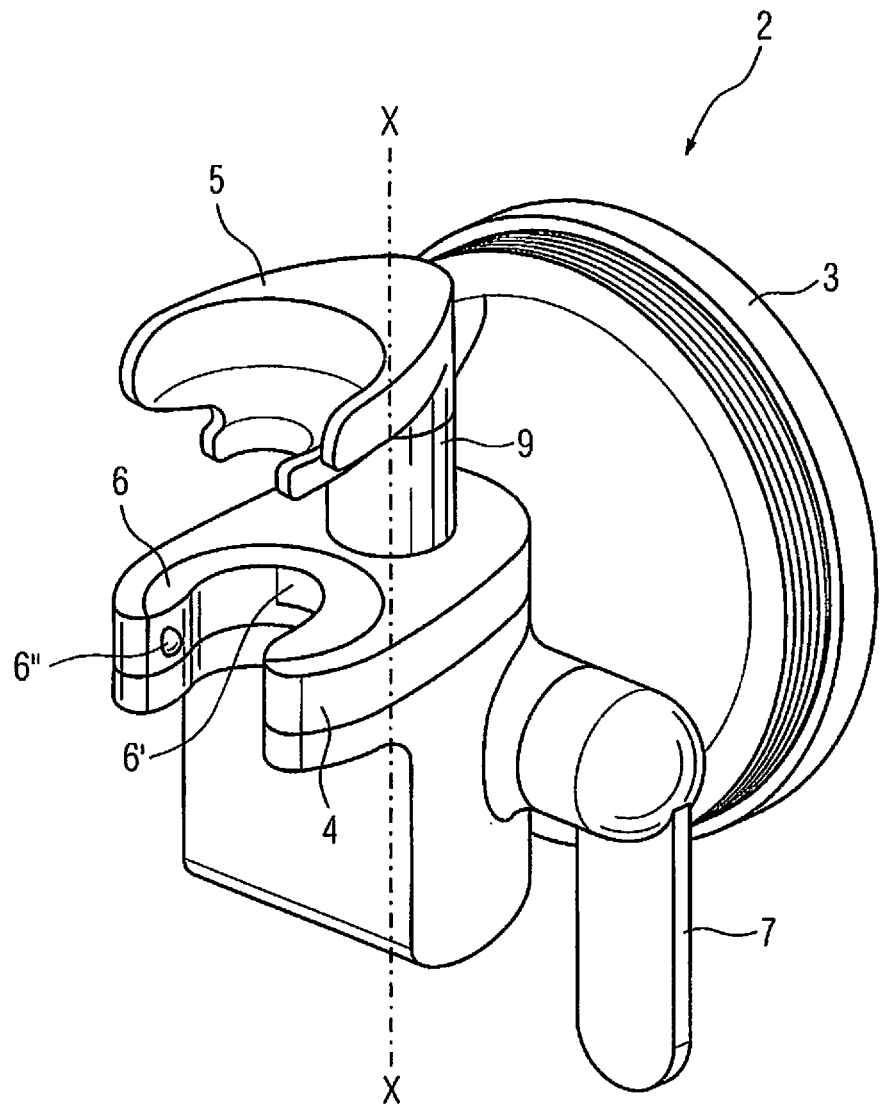
FIG. 3: a three-dimensional diagram of the apparatus according to the invention.

FIG. 3 shows a three-dimensional diagram of the apparatus according to the invention [2]. It consists of a first holder [4] for accommodating a connecting device [8], a second holder [5] for accommodating a vial [1], and actuating means [7] and a connecting device [8].

An actuating means [7] is connected to a lift rod [9] to which the second holder [5] is attached. The actuating means [7] can serve to move the lift rod [9] and the second holder [5] in an axis X.

A rotary disk is integrated [6] into the first holder. The connecting device [8] is secured in same by means of an undercut [6'] so that it is secured in the vertical direction and in the horizontal direction by means of catch noses [6"].

In one embodiment, the apparatus according to the invention may be permanently integrated into or detachably attached to a medical technical treatment unit, preferably an infusion device or an extracorporeal treatment unit, in particular a hemodialysis machine, by means of a machine holder [3].

The apparatus may thus be used in a medical technical procedure, in particular in a method for infusion or extracorporeal treatment, preferably in a hemodialysis process.

It has both rigid elements such as, for example, the connecting device [8] and soft elements such as, for example, the gasket [17]. The rigid material is preferably made of a polymer suitable for this purpose, such as polycarbonate (PC), polypropylene (PP), polyethylene (PE), polystyrene (PS), polyvinylchloride (PVC), polyethylene terephthalate (PET), polybutylene terephthalate (PBT), acrylonitrile-butadiene-styrene (ABS) and copolyester.

The soft material consists of a suitable elastic material, preferably an elastomer such as, for example, silicone rubber, styrene-ethylene-butylene-styrene (SEBS), styrene-ethylene-propylene-styrene (SEPS), styrene-isoprene-styrene (SIS), styrene-butadiene-styrene (SBS), polyurethane (PU), polyisoprene, thermoplastic elastomer (TPE), natural rubber (NR) and latex.

Figure 4A:
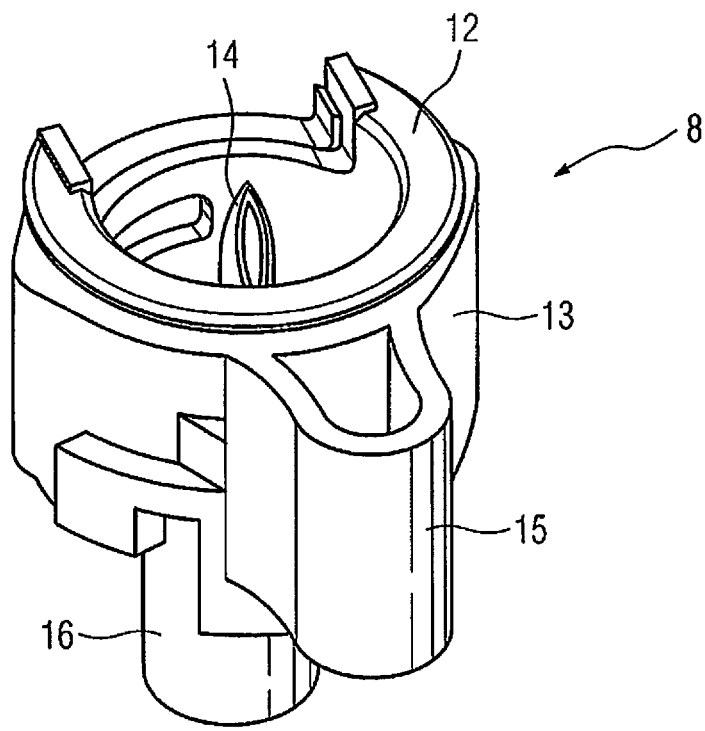
FIG. 4a: a three-dimensional diagram of the connecting device with closed flow paths.
Figure 5A:
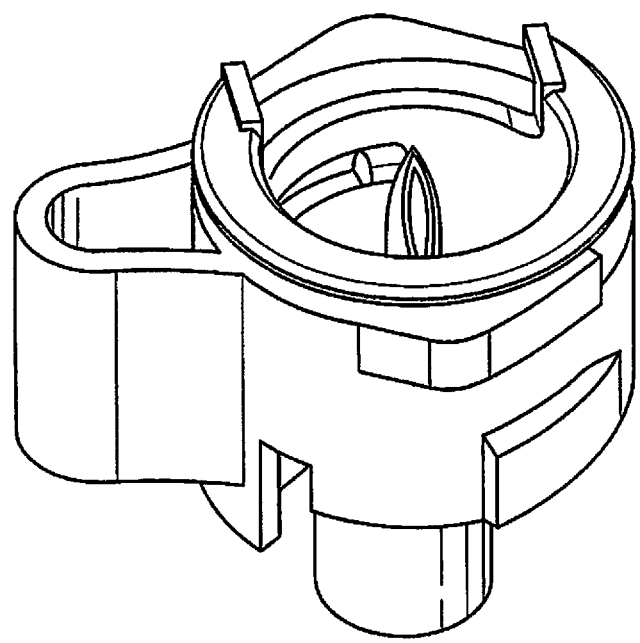
FIG. 5a: a three-dimensional diagram of the connecting device with open flow paths.

FIGS. 4a and 5a show a three-dimensional diagram of the connecting device [8] with both closed and opened flow paths.

Figure 4B:
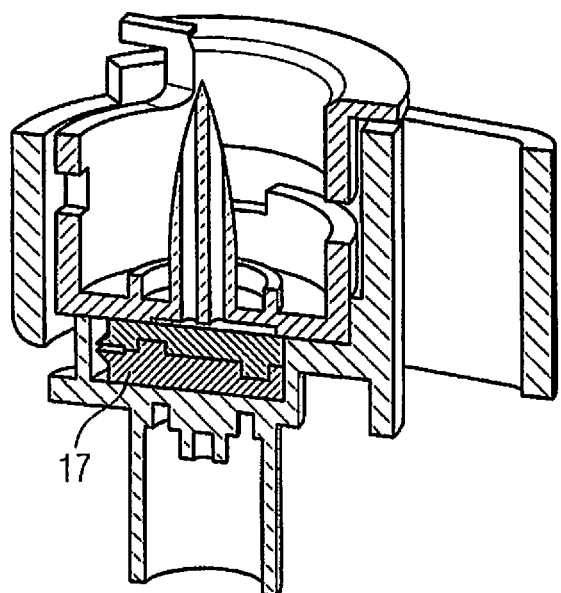
FIG. 4b: a three-dimensional diagram of the connecting device with closed flow paths in a longitudinal section.
Figure 5B:
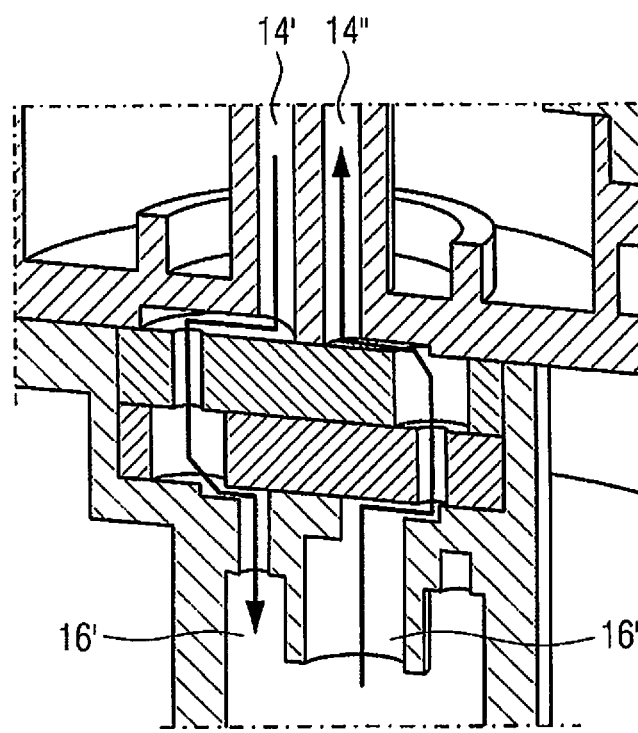
FIG. 5b: a three-dimensional diagram of the connecting device with open flow paths in a longitudinal section.

FIGS. 4b and 5b show a three-dimensional diagram of the connecting device [8] with both closed and opened flow paths in a longitudinal section.

FIGS. 4a/b and 5a/b show that the connecting device [8] consists of an annular housing [13] with an engagement surface [15], an inside part [12] which is also annular, a puncture device [14], a gasket [17] and a tube connection [16].

The housing [13] of the connecting device [8] is designed so that it can rotate about the inside part [12] in the function of a valve. The housing [13] can be guided securely and easily to the engagement surface [15], i.e., without applying any great force, around the inside part [12] during rotation.

Since vials [1] are made primarily of a material that is rigid, the volume of the contents transferred when transferring the contents of one vial [1] into a container or into a fluid line must be replaced, so that the flow does not stop. The puncture device [14] of the apparatus according to the invention [2] must therefore have two line paths. A first line path [14'] serves to transfer the contents of the vial [1] into a container or into a fluid line, while a fluid, preferably a gas, can flow into the vial [1] over a second line path [14"]. The contents of the vial [1] flowing out are therefore replaced, which thus prevents the development of a vacuum that would cause the flow to stop. The puncture device [14] may be designed in the form of two separate hollow needles, cannulas or spikes, preferably in the form of a double-lumen spike.

The connecting device [8] is also designed so that a cover [29] can be placed tightly on the puncture device [14]. It may preferably be made of an elastic material, so that it is compressed in connecting a puncture vial [1] and it releases the puncture device [14], returns back to its starting position in disconnecting and covers the puncture device [14] once again. By tightly covering the puncture device [14], contamination from the environment can be prevented.

Figure 10:
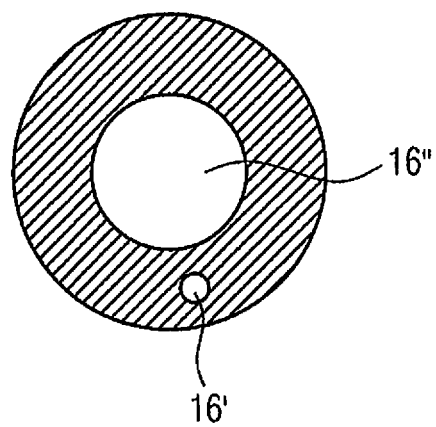
FIG. 10: a schematic diagram of the double-lumen tube.

The line paths of the puncture device [14] are continued in the hose connection [16] as the first flow path [16'] for a fluid [1] flowing out of the vial [1] and as the second flow path [16"] for a fluid flowing into the vial [1]. Ideally a double-lumen tube, such as that shown in FIG. 10, may be connected at this point.

In a three-dimensional diagram of the inside part [12] of the connecting device [8] of the apparatus according to the invention [2], FIG. 6 shows the first flow path [16'] for the contents of the vial [1] and the second flow path [16"] for a fluid flowing into the vial [1] and shows the contours of the gasket [22]. The sealing contours [22] serve to provide a defined seal of the flow paths so that the flow paths are completely surrounded during the rotation of the housing [13] about the inside part [12] in both the opened and closed states of the connecting device [8], thereby ensuring imperviousness.

FIG. 7 shows a three-dimensional diagram of the gasket [17] of the connecting device [8]. The gasket [17] serves to provide a fluid-tight connection between the inside part [12] and the housing [13].

In preferred embodiment, as illustrated in a three-dimensional diagram in FIGS. 7a and b, the gasket [17] consists of a first half [17'] and a second half [17"], which are designed to correspond to one another so that each half has a centering hole [18], a centering pin [19] and in a particularly preferred embodiment, a valve seat [20] and valve flap [21]. The type of valves and different possibilities with respect to the embodiment and/or functioning are known from the prior art and are described in detail in particular for use in a device for transferring liquids from vials, for example, in the International Patent Application WO 2011/141200 A1, the content of which is herewith incorporated into the present description, and therefore they will not be explained further at this point.

Figure 8A:
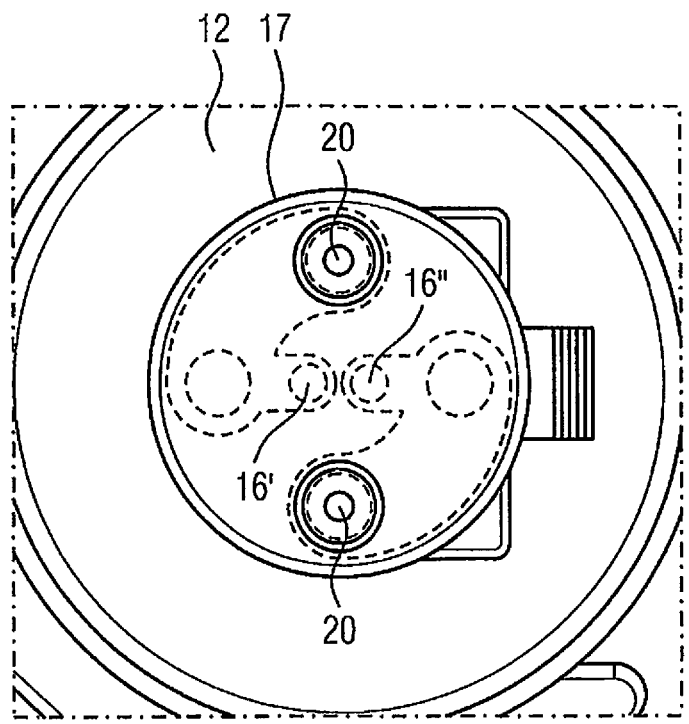
FIG. 8a: a schematic diagram of the inside part of the connecting device with the gasket attached in the closed state.
Figure 8B:
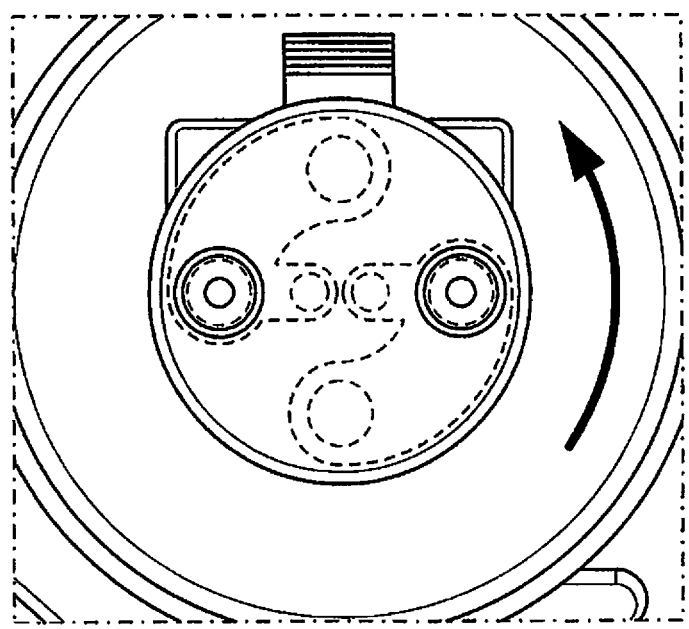
FIG. 8b: a schematic diagram of the inside part of the connecting device with the gasket attached in the open state.

The gasket [17] also rotates on the inside part [12] with the rotation of the housing [13]. FIG. 8a shows a schematic diagram of the inside part [12] of the connecting device [8] with the gasket [17] attached, shown in the closed state; FIG. 8b shows a schematic diagram of the inside part [12] of the connecting device [8] with the gasket [17] attached, shown in the open state.

Figure 9:
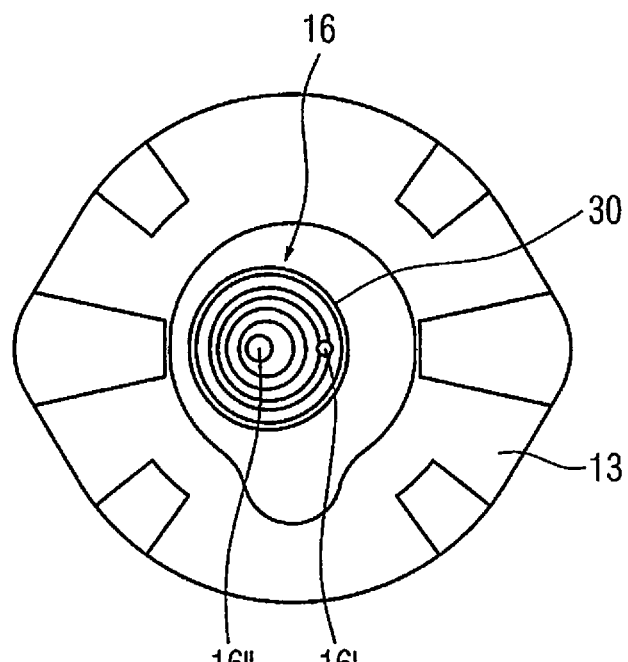
FIG. 9: a view of the housing with the tube connection in a schematic diagram.

FIG. 9 shows a view of the housing [13] with the tube connection [16] shown schematically. Ideally the housing [13] has defined connecting contours [30] on the tube connection [16] in a special embodiment in order to conduct fluids flowing in or out through the connecting device [8] in such a manner that a double-lumen tube can be connected independently of its angular position.

FIGS. 11a-d show a three-dimensional diagram of starting operation of the apparatus according to the invention [2].

Before starting operation of the apparatus according to the invention [2], the connecting device [8] to which a fluid line or a container is connected is inserted into the rotary disk [6] integrated into the first holder [4]. In doing so the connecting device [8] is secured in its vertical direction by the undercut in the rotary disk [6'] and is secured in the horizontal direction by catch noses [6"].

Figure 11A:
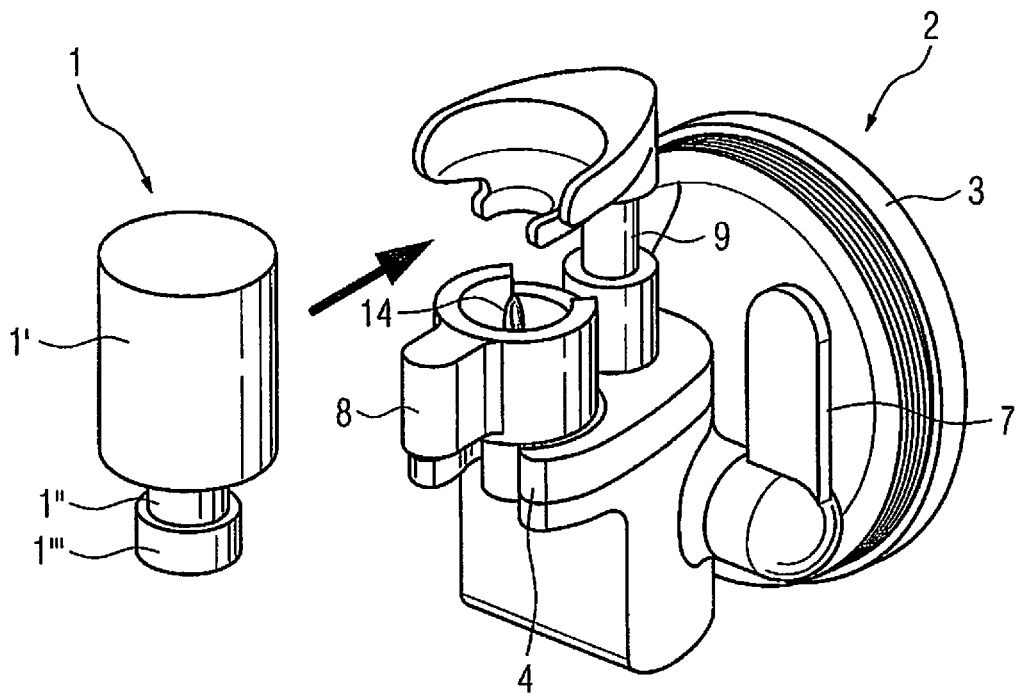
FIGS. 11a-d: a three-dimensional diagram of the process steps (starting operation of the apparatus according to the invention) of inserting a standard commercial vial and the connecting device up to the stage of opening the flow paths of the connecting device.

FIG. 11a shows the apparatus according to the invention [2] with the connecting device [8] inserted and a standard commercial vial [1] prior to insertion.

A standard commercial vial [1] consists of a body [1'], a neck [1"] and head [1'"]. The head [1'"] has a closure which may be designed as a stopper or a membrane and is attached to the neck [1"] by a flanged edge.

Figure 11B:
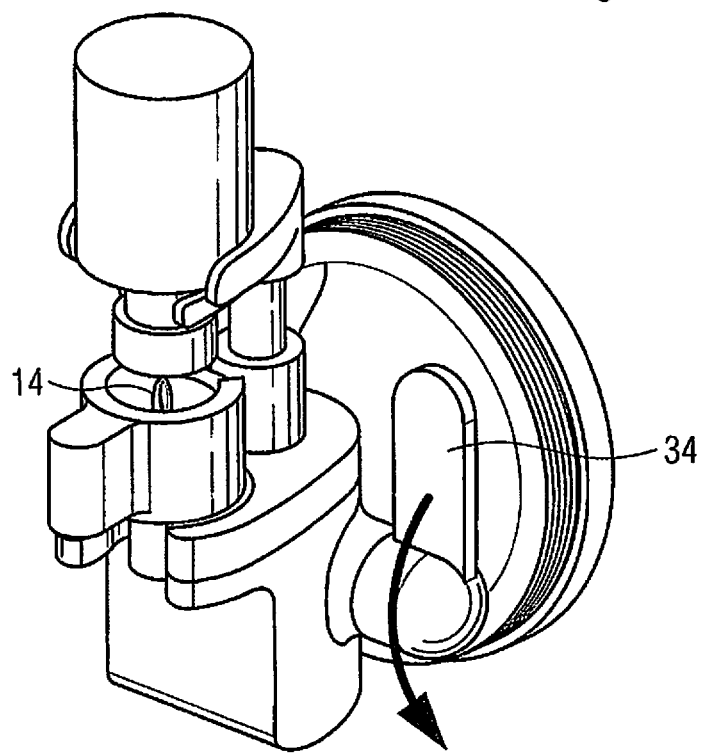

The vial [1] is inserted into the apparatus according to the invention [2] where it is pushed into the second holder [5] with its neck [1"], so that the head [1'"] of the vial [1] is directly opposite the connecting device [8]. This is shown in FIG. 11b.

Figure 11C:
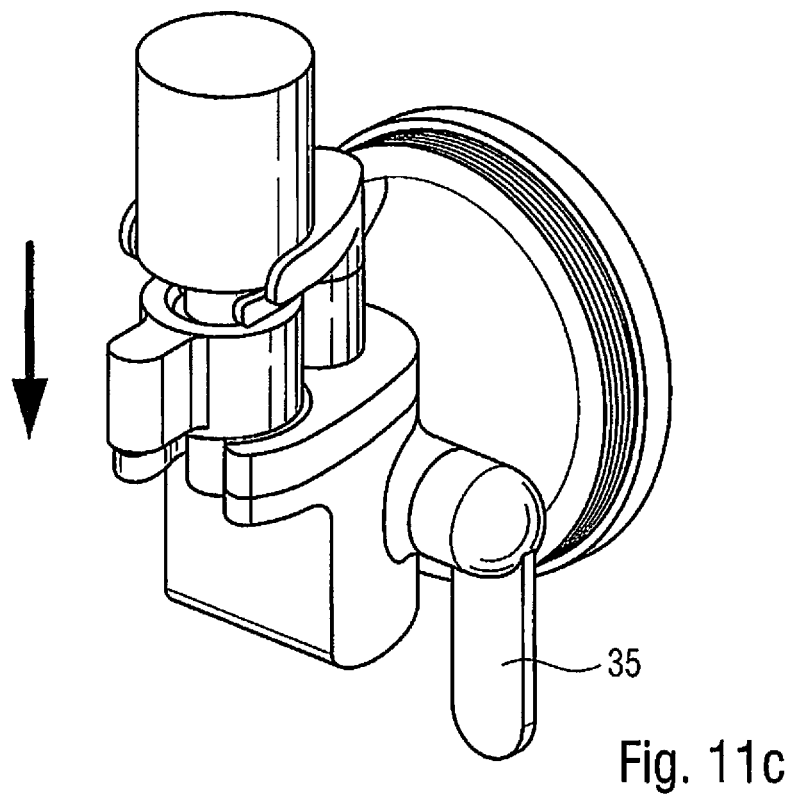

By moving the actuating means [7] which is connected to the lift rod [9] of the apparatus according to the invention [2], from a first position [34] into a second position [35], as shown in FIG. 11c, the vial [1] is moved in an axis X to the connecting device [8]. In doing so, the septum of the vial [1] is perforated by the puncture device [14], which completely enters the vial [1] when in the second position [34] of the actuating means [7], so that the first line path [14'] and a second line path [14"] open into the interior of the vial [1].

Figure 11D:
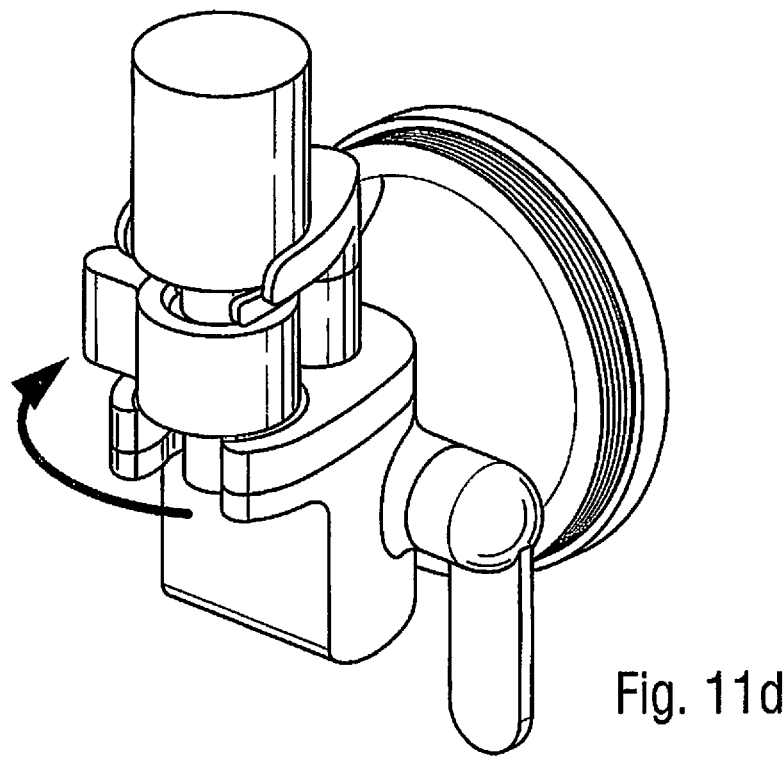

FIG. 11d shows the opening of the connecting device [8] by rotation of the housing [13] about the inside part [12]. The rotation is preferably by 90° to one side of the apparatus according to the invention [2]. By securing of the connecting device [8] by catch engagement of the housing [13] in the undercut [6'] and the catch noses [6"] of the rotary disk [6], the latter is also moved in the rotation of the housing [13]. The inside part [12] abuts against the second holder [5] and/or together with it forms a form-fitting closure and is thus secured in its starting position.

The rotation of the rotary disk [6] has two effects: first it reliably prevents removal of the opened connecting device [8] and secondly the connecting device [8] is secured in its vertical position.

By rotating the housing [13] about the inside part [12] back into its central starting position, the connecting device [8] is closed again. The rotary disk [6] also rotates back into its starting position in synchronization with the housing [13].

If the transfer of the contents of the vial [1] is to be terminated, the actuating means [7] is moved back from the second position [35] into the first position [34]. The lift rod [9] of the apparatus according to the invention [2], to which the second holder [5] is attached, moves together with it and separates the vial [1] and the connecting device [8] from one another. The two parts can then be removed.

In another embodiment, it is conceivable for the vial [1] and the connecting device [8] to be removed in the connected state when the connecting device [8] is closed. This permits a faster and more convenient dismantling of the apparatus according to the invention [2] after it has been used.

Determined by the interaction of the individual components, the device according to the invention [2] can be operated exclusively in a defined sequence of individual steps. Thus, for example, the opening and closing of the flow paths of the connecting device [8] are possible only if a vial has been inserted. Removal of the vial [1] is in turn possible only when the connecting device [8] is in the closed position.

Insertion of the vial [1] and the connecting device [8] into the apparatus according to the invention [2], combining all the parts by activation of the actuating means [7] and opening and/or closing the connecting device [8] are all actions that can be performed with one hand.

Figure 12A:
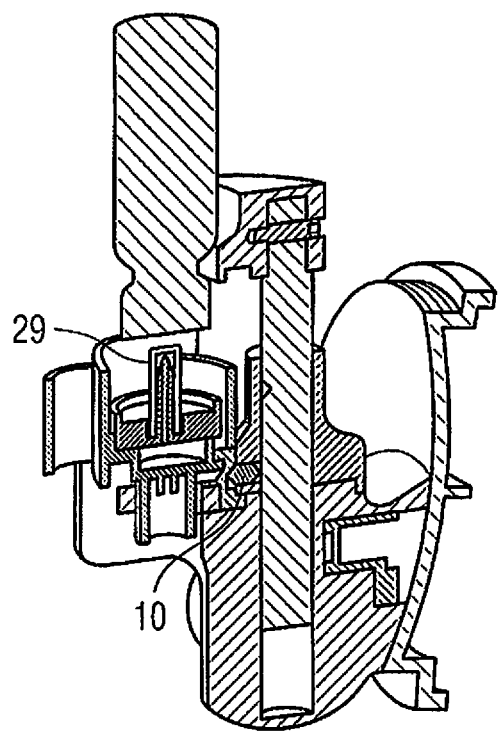
FIG. 12a: a diagram of the apparatus according to the invention in a longitudinal section with the vial disconnected.

FIG. 12a shows the apparatus according to the invention in a longitudinal section with the vial [1] disconnected and with the connecting device [8] closed. If the actuating means [7] is in its first position [34], an adjusting element [10] secures the rotary disk [6]. Unintentional rotation of the rotary disk [6] and thus of the housing [13] of the connecting device [8] is thus prevented.

Figure 12B:
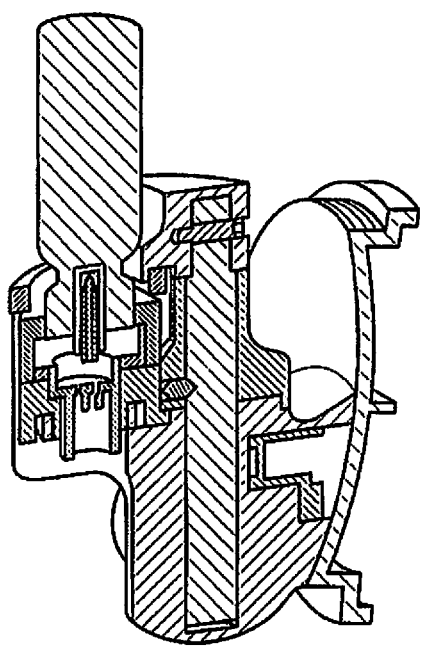
FIG. 12b: a diagram of the apparatus according to the invention in a longitudinal section with the vial connected.

FIG. 12b shows an apparatus according to the invention in a longitudinal section with the vial connected and the connecting device [8] opened. If the actuating means [7] is in its second position [35], then an adjusting element [10] secures the lifting rod [9]. This prevents unintentional separation of the vial [1] from the connecting device [8].

The adjusting element thus supports holding of the vial and the connecting device tightly, securely and accurately.

Figure 13A:
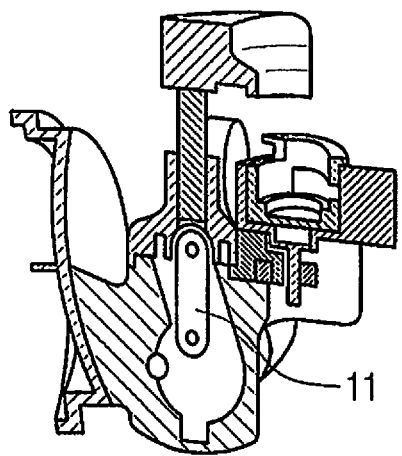
FIGS. 13a-c: a diagram of the mechanical features of the apparatus according to the invention in a sectional view during connection of the vial.
Figure 13B:
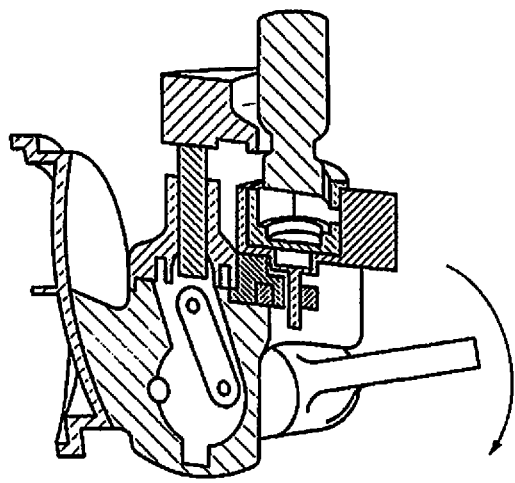
Figure 13C:
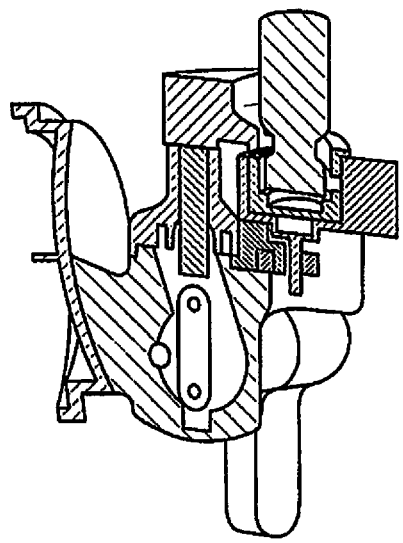

FIG. 13a-c shows the individual steps of the mechanical aspects of the apparatus according to the invention in multiple sectional views during the connection of a vial.

A mechanical translation takes place in the interior of the apparatus according to the invention [2], for example, in the form of a toggle lever [11] or a gearwheel, which serves to transmit the force. This greatly reduces the force to be expended by the personnel in bringing the vial [1] and the connecting device [8] together, i.e., to 50N in the individual case, and handling is facilitated.

Figure 14:
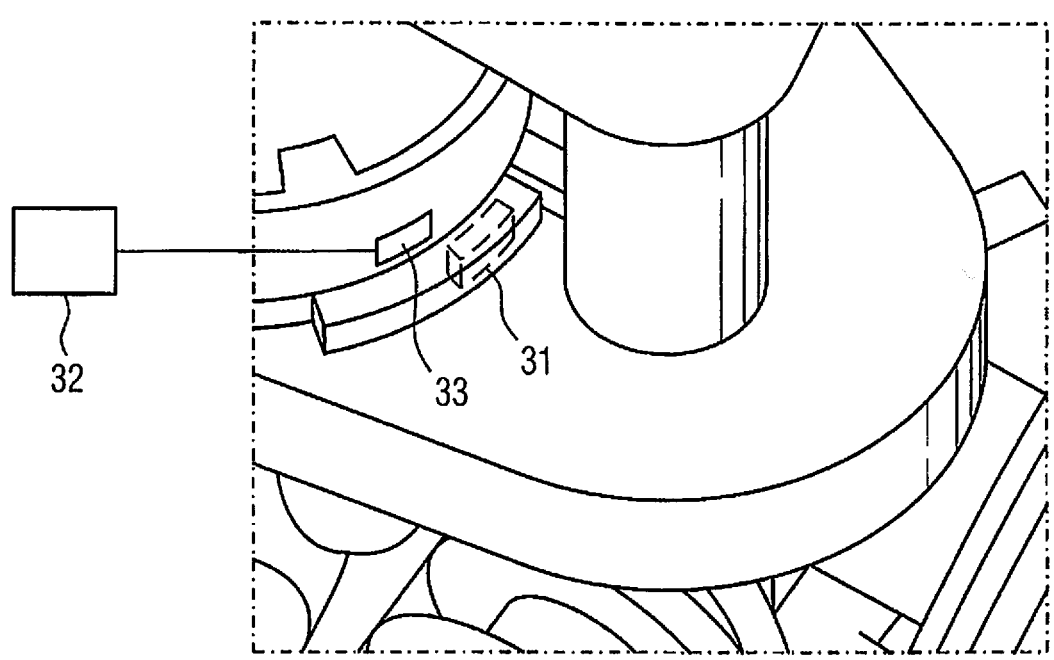
FIG. 14: a three-dimensional diagram of a detail of the apparatus according to the invention.

FIG. 14 shows in a detail of the apparatus according to the invention [2] a sensor [31], for example, a Hall sensor which detects the position of the connecting device [8] by means of a magnet [33]. In a particular embodiment, the apparatus according to the invention has an evaluation unit [32] as the external additional device or is integrated into the dialysis machine which recognizes the position of the vial [1] by means of at least one sensor [31] and/or the position of the connecting device [8] and/or the opening of the connecting device [8] and can provide an acknowledgement to the dialysis machine or to the user, if needed.

However, it is also conceivable that there is an indication of whether the connecting device [8] is opened or closed by means of a window in the housing of the connecting device [8], which enables a view to an optical character on the inside part [12], for example, a color or a symbol, depending on the position of the housing [13].

The invention being thus described, it will be apparent that the same may be varied is many ways Such variations are not to be regarded as a departure from the spirit and scope of the invention, and all such modifications as would be recognized by one skilled in the art are intended to be included within the scope of the following claims 1 vial
1' body of the vial
1" neck of the vial
1''' head of the vial
2 device for connecting a vial
3 machine holder
4 first holder
5 second holder
6 rotary disk
6' undercut
6" catch noses
7 actuating means
8 connecting device
9 lift rod
10 adjusting element
11 toggle lever
12 inside part of the connecting device
13 housing of the connecting device
14 puncture device
14' first line path
14" second line path
15 engagement surface
16 tube connection
16' flow path for contents of vial
16" flow path for fluid
17 gasket
17' first half of gasket
17" second half of gasket
18 centering hole
19 centering pin
20 valve seat
21 valve flap
22 sealing contours
23 tube set
24 drip chamber
25 infusion container
26 pump
27 dialyzer
28 injection site
29 cover
30 connecting contours
31 sensor
32 evaluation unit
33 magnet
34 first position of the actuating means
35 second position of the actuating means
A feed point for the arterial leg
B feed point for the arterial leg
C feed point for the drip chamber
D feed point for the venous leg

What is claimed is:

1. A device for connecting a vial to a container or to a fluid line, and for transferring the contents of the vial to the container or to the fluid line, said device comprising:
   a connecting device, including an annular housing, flow paths, an inside part having a puncture device, and a tube connection;
   a first holder configured to accommodate the connecting device;
   a second holder configured to accommodate the vial; and
   an actuator, with the actuator being connected to a lift rod to which the second holder is attached, for moving the vial from a first position a punctured position,
   the annular housing of the connecting device being rotatable about the inside part so as to function as a valve, with the flow paths of the connecting device being openable and closeable by rotation of the annular housing.

2. The device according to claim 1, wherein the first holder has a rotary disk.

3. The device according to claim 2, wherein the rotary disk has at least one undercut and catch noses for accommodating the connecting device, and wherein the connecting device is secured by the undercut in a vertical direction and by the catch noses in a horizontal direction.

4. The device according to claim 1, wherein when the vial is connected, the inside part is mechanically secured by the second holder in a starting position thereof.

5. The device according to claim 2, wherein an adjusting element secures the rotary disk when the vial is disconnected, and thus prevents the annular housing from rotating, and when the vial is connected and the connecting device is open, the adjusting element secures the lift rod and thus prevents the vial and the connecting device from being separated.

6. The device according to claim 1, wherein the connecting device has a gasket with at least one valve.

7. A method of connecting a vial to a container or to a fluid line, and of transferring the contents of the vial into the container or the fluid line, with a device that includes a connecting device having an annular housing, a flow path, an inside part having a puncture device, and a tube connection, a first holder, a second holder, and an actuator connected to a lift rod to which the second holder is attached, said method comprising the following steps:
   catch engaging the connecting device in the first holder;
   catch engaging the vial in the second holder;
   combining the vial and the connecting device by activating the actuator to move the lift rod so as to move the vial from a first position to a punctured position, with the puncture device puncturing a septum of the vial;
   opening the flow path by rotation of the annular housing of the connecting device about the inside part;
   closing the flow path by rotation of the annular housing of the connecting device about the inside part;
   activating the actuator to disconnect the vial and the connecting device; and
   removing the vial from the second holder and the connecting device from the first holder.

8. The method according to claim 7, wherein in combining the vial and the connecting device, the actuator moves the lift rod, which moves the second holder and the vial in an axis X toward the connecting device.

9. The method according to claim 7, wherein when opening the flow path by rotation of the annular housing, a rotary disk accommodating the annular housing also rotates, and the inside part remains in a starting position thereof, due to a form-fitting connection with the second holder.

10. A tube set or cassette set having a device according to claim 1.

11. A medical technical treatment unit having a device according to claim 1.

12. A use of a device according to claim 1 in a medical technical method.

13. An evaluation unit for a device according to claim 1, wherein the evaluation unit employs at least one sensor to detect a position of the vial and/or a position of the connecting device and/or the opening of the connecting device.

14. The medical technical treatment unit according to claim 11, wherein the medical technical treatment unit is an infusion device or an extracorporeal treatment unit.

15. The medical technical treatment unit according to claim 14, wherein the extracorporeal treatment unit is a hemodialysis machine.

16. The use of the device according to the medical technical method of claim 12, wherein the method is for an infusion or an extracorporeal treatment.

17. The use of the device according to the medical technical method of claim 16, wherein the extracorporeal treatment is a hemodialysis process.

* * * * *